United States Patent

Wagatsuma et al.

[11] Patent Number: 5,849,503
[45] Date of Patent: Dec. 15, 1998

[54] MUTANT PROTEINS OF HUMAN DNA TOPOISOMERASE I

[75] Inventors: Masako Wagatsuma, Tokyo; Noriko Kurita, Osaka, both of Japan

[73] Assignee: Nippon Hoechst Marion Roussel Limited, Tokyo, Japan

[21] Appl. No.: 663,112
[22] PCT Filed: Dec. 28, 1994
[86] PCT No.: PCT/JP94/02280
  § 371 Date: Nov. 26, 1996
  § 102(e) Date: Nov. 26, 1996
[87] PCT Pub. No.: WO95/18218
  PCT Pub. Date: Jul. 6, 1995

[30] Foreign Application Priority Data

Dec. 28, 1993 [JP] Japan .................................. 5-349029

[51] Int. Cl.$^6$ .............................. G01N 33/53; C12N 9/90
[52] U.S. Cl. ........................... 435/7.1; 435/183; 435/233
[58] Field of Search ............................. 530/350; 435/183, 435/172.3, 233, 320.1, 252.33, 7.1, 91, 252.3; 536/23.5

[56] References Cited

U.S. PATENT DOCUMENTS 5,070,192 12/1991 Earnshaw et al. ..................... 536/23.5
5,541,291 7/1996 Keene et al. ............................ 530/350

OTHER PUBLICATIONS

J.H. Shero et al., Science, 231:737–740 (1986).
P. D'Arpa et al., Proc. Natl. Acad. Sci., USA 85(8):2543–2547. (1988).
R.M. Lynn, et al., Proc. Natl. Acad. Sci., USA 86 (10):3559–3563. (1989).
Benton, W.D., and Davis, R.W., Science, 196(4286):180–182. (1977).
Sanger, Proc. Natl. Acad. Sci., USA, 74:(12):5463 (1977).

*Primary Examiner*—John L. LeGuyader
*Attorney, Agent, or Firm*—Finnegan, Henderson, Farabow, Garrett & Dunner, L.L.P.

[57] ABSTRACT

Mutant proteins of human DNA topoisomerase I having an amino acid sequence in which tyrosine at the 592nd position of human DNA topoisomerase I is lacking or replaced with phenylalanine and which contains at least 30 amino acids in succession of the amino acid sequence subsequent to the 542nd amino acid of human DNA topoisomerase I.

Above described mutant proteins react with anti-Scl-70, antibody in the sera of autoimmune disease patients of diffuse scleroderma and can be produced by genetic engineering using *E. coli*, and therefore they are useful as a diagnostic agent of scleroderma.

19 Claims, 6 Drawing Sheets

LANES 1-29: SERA OF Scl-70 POSITIVE PATIENT
LANE 30: POLYCLONAL ANTIBODY (pSEM)
LANE 31: NORMAL SERA

LANE 1: JUST BEFORE IPTG ADDITION
LANE 2: 4 HOURS AFTER IPTG ADDITION
LANE 3: 18 HOURS AFTER IPTG ADDITION

FIG. 5

A: 4 HOURS AFTER IPTG ADDITION
B: 18 HOURS AFTER IPTG ADDITION
LANES 1 TO 6: CLONE NUMBERS
P: POSITIVE-CONTROL
N: NEGATIVE-CONTROL

FIG. 6

MUTANT PROTEINS OF HUMAN DNA TOPOISOMERASE I

BACKGROUND OF THE INVENTION

1. Field of the Invention

This invention relates to novel mutant proteins of human DNA topoisomerase I. These mutant proteins are preferably produced by genetic engineering and useful for a diagnosis of autoimmune diseases and for analysis of topological interconversion of genes.

2. Description of the Prior Art

The autoantibodies against various nuclear antigens are detected in the sera of patients with autoimmune diseases, and it is possible to diagnose autoimmune diseases by detecting these autoantibodies.

It is known that, among these autoantibodies, the autoantibodies against a nuclear antigen, Scl-70 having a molecular weight of 70 kD, are detected in sera of many patients with an autoimmune disease named diffuse scleroderma. In recent years it has been demonstrated that Scl-70 is a 70 kD-molecular-weight protein of the C-terminal fragment of DNA topoisomerase I (J. H. Sero et al., 1986, Science, Vol. 231, pp. 737–740). DNA topoisomerases catalyze the breaking and rejoining of DNA strands in a way that allows the strands to pass through one another, thus altering the topology of DNA. There exist two kinds of DNA topoisomerases, Type I and Type II. Type I cleaves a single chain DNA while Type II cleaves a double-chain DNA.

The topological interconversion is brought about by these DNA topoisomerases I and II, which are necessary for the transcription from DNA to RNA and for replication of DNA. These DNA topoisomerases I and II are also essential proteins for cell proliferation and functional maintenance such as protein synthesis. In particular, Scl-70, namely, 70 kD-molecular-weight protein of the C-terminal fragment of human DNA topoisomerase I, is useful for a diagnosis of autoimmune diseases such as diffuse scleroderma. However, it is not commercially feasible to extract and purify human DNA topoisomerase I from natural materials due to scarce content of the protein in organisms. It is preferably by genetic engineering that the enzyme is practically produced.

The cDNA of human DNA topoisomerase I was cloned by P. D'Arpa in 1988 (Proc. Natl. Acad. Sci., USA, Vol. 85, pp. 2543–2547). However, production of a sufficient amount of the targeted recombinant protein was unsuccessful. A trial was made to express human DNA topoisomerase I by integrating it into a conventional expression vector in E. coli according to conventional genetic engineering methods. A large amount of the enzyme production in E. coli caused inhibition of the transcription of the E. coli DNA itself and caused inhibition of DNA replication. Thus, growth of the E. coli was inhibited, and death of the E. coli was observed.

DETAILED DESCRIPTION OF THE INVENTION

The present invention provides for mutant proteins of human DNA topoisomerase I which are preferably produced by genetic engineering. It is estimated that the active site of human DNA topoisomerase I is tyrosine (Tyr) at amino acid 723 (Proc. Natl. Acad. Sci., 1989, Vol. 86, pp. 3559–356). Moreover, a mutant protein lacking 95 amino acids at terminal fragments and 723-phenylalanine (Phe) whose active also inhibited the growth of E. coli, and failed to produce a sufficient amount of the mutant protein. Then, upon producing a mutant protein of human DNA topoisomerase I (FF mutant hereinafter, shown in SEQ ID NO.:1 of the Sequence Listing) by substituting Tyr at the 592nd amino acid with Phe, FF mutant reacted sufficiently with anti-Scl-70, autoantibodies in the sera of autoimmune disease patients. In addition the production of FF mutuant in E. coli was found very high, which led to the completion of the invention.

Further, it was found that the mutant protein of human DNA topoisomerase I which consists of Ala at the 96th amino acid to Phe at the 765th amino acid, Tyr at the 723rd (i.e., the amino acid of the wild type protein) and substituting Tyr at the 592nd amino acid with Phe (FY mutant hereinafter) was recovered in a large quantity at 4 to 5 hours after induction of transformed E. coli by reagents. FY mutant as well as FF mutant has antigenicity and is produced from the cultured E. coli, and can be utilized as a diagnostic reagent.

The fragment peptide of human DNA topoisomerase I which contains at least 30 and preferably 40 or more amino acids in succession from the amino acid sequence from proline (Pro) at the 542nd, amino acid if Tyr at the 592nd amino acid of human DNA topo-isomerase I is lacking or replaced with Phe, contains epitopes which anti-Scl-70 autoantibody recognizes (refer to Example 5), and can also be utilized as a diagnostic reagent. Examples of peptide fragments are also contained in the mutant proteins of this invention. The ES mutant protein (ES mutant) consists of Ala at the 96th amino acid through Arg at the 590th amino acid of each wild type human DNA topoisomerase I. The SR mutant protein (SR mutant) consists of Thr at the 591st amino acid through Phe at the 765th amino acid and the Tyr residues at the 592nd and the 723rd amino acids which are replaced with Phe, and the mutant protein consisting of Pro at the 542nd amino acid through Phe at the 765th amino acid and the Tyr at the 592nd and the 723rd amino acid which are replaced with Phe are examples, in addition to FF mutant and FY mutant.

Further, the mutant proteins of human DNA topoisomerase I and their fragments according to the present invention also include those of the converted amino acids by deficiency, replacement addition or combination thereof provide that change in its antigenicity is not caused.

By using either FF mutant or FY mutant of the present invention, an antoimmune disease assay kit can be produced according to a conventional method. The analysis methods that can be used are ELISA, RIA and Latex Agglutination wherein an autoantibody in a specimen is detected by binding either FF mutant or FY mutant on an immobilized phase of plastic or glass and using these as antigens according to immunological antigen-antibody reaction. Also, the autoimmune disease diagnosed according to the present invention can be used for diagnosis of autoimmune diseases in which autoantibodies against Scl-70 are detected in the sera. A representative autoimmune disease is diffuse scleroderma.

EXAMPLE

This invention shall be more illustratively explained by way of the following Examples.

Example 1

Cloning of cDNA encoding human DNA topoisomerase I

1. According to the method by Benton Davis et al. (Science 1977, Vol. 196, p. 180), a single colony of E. coli LE392 (purchased from Promega Co.) was cultured for 5 hours in LS culture medium (10 g polypeptone, 5 g yeast extract, 2.5 g NaCl/1 L) which were added 0.02% maltose and 10 mM $MgSO_4$, and 0.3 ml of the culture was distributed into a test-tube, and 40 µl of human placenta-derived cDNA library HL1008 (purchased from Clontech Lab. Co.) equivalent to $3.5 \times 10^5$ P.F.U. (plaque forming unit) diluted with λdil (86 mM NaCl, 100 mM Tris-HCl pH 7.4, 0.001% gelatin, 1 mM $MgCl_2$) was added and then added with 10 ml λtop agarose at 60° C. (BACTOTRYPTONE 10 g, NaCl 5 g, agarose 5 g/L:10 mM $MgSO_4$), after agitation flown onto LS agarose plate (15 cm diameter). After the agarose was solidified, the plate was cultured in an incubator at 37° C. for 6 hours, and then moved to 4° C.

2. For purposes of transferring the plaque developed on the agarose to a nitrocellulose filter (purchased from Schleicher & Schwell Co.), the filter was placed on the agarose, and pulled off the agarose after 2.5 minutes, and dried for 10 minutes at room temperature. Then, the filters were treated for 2.5 minutes each with alkali denaturing solution (0.5N NaOH/1.5M NaCl), neutralizing solution (0.5M Tris-HCl, pH 7.5) and 2×SSC (0.15M NaCl, 0.015M $Na_3$ citrate-$2H_2O$), and dried at 37° C. for 30 minutes. The filters were then further heat-treated in an oven at 80° C. for 2 hours.

3. The above described filters were soaked with a prehybridization solution (50% formamide, 6×SSC, 5×Denhardt, 50 mM Hepes pH 7.0, 80 µg/ml ssDNA) at 40° C. for 4 to 5 hours. Then, by using 12 ml of the same solution containing $1 \times 10^7$ cpm of probe labelled with $^{32}p$, 10 sheets of filters were sealed in a hybridization bag, incubated at 40° C. for 20 hours. After the incubation, the filters were out, and after removed washed once with 2×SSC at room temperature for 15 minutes, and 3 times with 0.1×SSC/0.1% SDS at 42° C. for 15 minutes, were then air-dried and autoradiographed.

4. Labelling of probe

70 µCi (2.6 MBq) of $\gamma^{32}$ATP and T4 kinase were added to 50 pmole of synthesized DNA, reacted at 37° C. for 30 minutes in a reaction mixture (70 mM Tris-HCl, pH 7.6, 10 mM $MgCl_2$, 5 mM DTT, 1 mM EDTA). Free isotope was removed by a span column of Sephadex G50 (fine) (purchased from Pharmacia AB).

5. Isolation of single plaque

A plaque located at a position of signals on the autoradiogram was picked suspended in 500 µl of γdil, diluted as in Example 1-1 to obtain the plaque. The procedures as described in Example 1-2 and were repeated, and a single plaque was isolated.

6. Detection of insert size of phage DNA from a plaque

The isolated plaque was suspended in 200 µl of SM buffer (100 mM NaCl, 8 mM $MgSO_4$, 50 mM Tris-HCl, pH 7.5, 0.01% gelatin), diluted and use to infect 400 times, E. coli Y1090 (purchased from Stratagene Co.) to obtain a novel plaque. The novel plaque was suspended in 200 µl of SM buffer, to prepare a phage solution for PCR. 4 µl of the phage containing solution was added to 20 µl of PCR buffer (1 µM primer, 0.2 mM dNTP, 67 mM Tris-HCl, pH 8.8, 1 mM β-ME, 16.6 mM $(NH_4)_2SO_4$). The Reaction mixture was heated once for 5 minutes at 95° C., and then, for 35 cycles, the reaction mixture was heated for 1 minute at 94° C., then 2 minutes at 55° C. and then 3 minutes at 72° C. The size of the DNA obtained from the PCR reaction was examined by electrophoresis with 0.8% agarose gel, using ⅕ volume of the reaction mixture. Further, 3 µl of the solution after the PCR reaction was digested with Hind III, EcoRV, BstXI and XhoI, and then subjected to electrophoresis in the same manner as shown above, and the migration pattern was examined.

7. Preparation of phage DNA

After each 5 µl, 10 µl and 20 µl of the phage solution containing Scl-70 cDNA was used to infect 100 µl of E. coli LE 392. The bacteria-phage mixture was spread on agarose plate (8 cm in diameter), and incubated at 37° C. overnight. 4 ml of SM buffer was added per plate, which stood at room temperature for 2 to 3 hours. The buffer was transferred to a centrifugal tube of 15 ml, and centrifuged at 3,000 rpm for 10 minutes. 20 µg/ml of RNase and 20 µg/ml of DNase were added to the supernatant, and incubated at 37° C. for 30 minutes. The solution was centrifuged at 35,000 rpm at 4° C. for 45 minutes using a Hitachi RPS 40T rotor. The precipitate was suspended in 600 µl of sterilized distilled water, then transferred to an Eppendorf tube, and centrifuged for 5 minutes at 4° C. at 15,000 rpm. Next 100 mM of EDTA and 0.2% of SDS to 500 µl was added to the supernatant. The solution was extracted once with the same volume of phenol saturated with TE (10 mM Tris-HCl, pH 7.5, 1 mM EDTA), twice with ½ volume chloroform. Then, 250 mM NaCl and two volumes of ethanol were added to the solution, then incubated at −80° C. for 5 to 10 minutes, centrifugated at 15,000 rpm for 15 minutes and the precipitate was recovered. The precipitate was dissolved in 200 µl of sterilized distilled water resulting in a phage DNA solution.

8. Sub-cloning

60 µl of the phage DNA solution was digested with EcoRI in the 200 µl reaction mixture, extracted with phenol, fractionated by electrophoresis in 0.8% agarose, and a 3.5 kb EcoRI fragment was obtained by glass milk method. Namely, 200 µl of agarose fragment containing DNA was dissolved with 600 µl of NaI solution, by incubating at 55° C. for 3 minutes, 5 µl of the glass milk was added and incubated for 5 minutes on ice. The glass milk was precipitated by centrifugation at 15,000 rpm for 10 seconds, then the glass milk was washed with an ethanol/salt base washing solution for 2 to 3 times, 10 µl of water was added to the precipitate, incubated at 55° C. for 3 minutes. The DNA was recovered as an aqueous solution after centrifugation. This procedure was performed by using GENECLEAN Kit II (purchased from Funakoshi Co., Ltd.) (Glass Milk Method).

85 ng (1 µl) of pUC118 was added to 15 ng (equivalent to 3 µl) of the DNA, then 16 µl of TAKARA ligation A buffer (purchased from Takara Shuzo Co., Ltd.) and 4 µl of B buffer was added to the DNA solution, and incubated at 16° C. for 30 minutes.

10 µl of the ligation reaction mixture was mixed with 200 µl of Competant Cell (DH5α:purchased from Toyobo Co.), and stored on ice for 30 minutes. Then, after the mixture was incubated at 42° C. for 2 minutes, 800 μl of LS was added and incubated at 37° C. for 60 minutes. The upper solution was spread on an ampicillin plate (containing 0.1 mM Xgal 0.004% of isopropyl-1-thio-β-D-galactoside (IPTG)), and incubated at 37° C. overnight. The obtained clone p66 was subjected to further experiments.

Example 2

Production of FF Mutant Carrying Plasmid (pSEM•FF)

1. PCR Amplification of Fragment I

By using each 1 μM of Scl-70 $PR_1$ primer (SEQ ID NO.:2) and Scl-70 $PF_1$ primer (SEQ ID NO.:3), a PCR reaction mixture (200 μl) containing 0.5 ng of Scl-70/pUC118 clone p66-derived EcoRI/EcoRV 2.1 kb fragment was reacted at 95° C. for 1 minute, then at 55° C. for 2 minutes, and then at 72° C. for 2 minutes, and the reaction cycle was repeated 40 times. After completion of the reaction, the reaction mixture was extracted twice with 100 μl chloroform water saturated phenol and chloroform, and once with 200 μl of chloroform. Then, 200 mM of NaCl and 2.5 volume of ethanol was added to the reaction mixture, and stored at –20° C.

2. Digestion with Restriction Enzyme and Sub-Cloning

After digesting the PCR amplified fragment with Avr II and Nhe I, the fragment was phenol extracted and precipitation with ethanol were performed as described above. 6 μg of Scl-70/pUC118 clone p66 plasmid was digested with Avr II and Nhe I, Avr II-Nhe I fragment was fractionated by electrophoresis with 0.8% agarose gel, and the remaining 6.9 kb vector fragment was isolated by the glass milk method. After 32 ng of the vector fragment was ligated with 100 ng of a PCR amplified fragment by TAKARA ligation kit, 10 μl of the ligation mixture was mixed with 200 μl of competent cells of DH5α and the transformation was performed as described above. The nucleotide sequence of the obtained clone was analyzed by Sanger Method (Proc. Natl. Acad. Sci., 1977, Vol. 74, p. 5463) with N8 primer (SEQ ID NO.:4), and the clone, in which the 723rd amino acid Tyr therefore was substituted with Phe was named p66e.

3. Amplification of PCR Fragment II and Sub-Cloning

By using $PF_2$ primer (SEQ ID NO.:5) and $PR_2$ primer (SEQ ID NO.:6), after the PCR reaction was performed in 0.75 mM of $MgCl_2$ as with fragment I, the product was extracted with phenol and precipitated with ethanol, and the fragment was recovered. The fragment was digested with Nhe I and Spl I, and subjected to phenol extraction and ethanol precipitation. On the other hand, the p66e vector backbone was obtained by digesting with Nhe I and Spl I, and then, phenol extraction and ethanol precipitation were carried out. These DNA fragments were fractionated by electrophoresis is an 0.8% agarose gel. The 200 bp of the PCR fragment and the 6.9 kb band of the vector were recovered by the glass milk method. The two isolated DNA fragments were ligated and transformed by using 200 μl of competent cells of XL 1 blue (Strategene Co.). The nucleotide sequence of the resulting clone was analyzed and the clone was named p66FF.

4. Construction of Expression Vector

Figure 1:
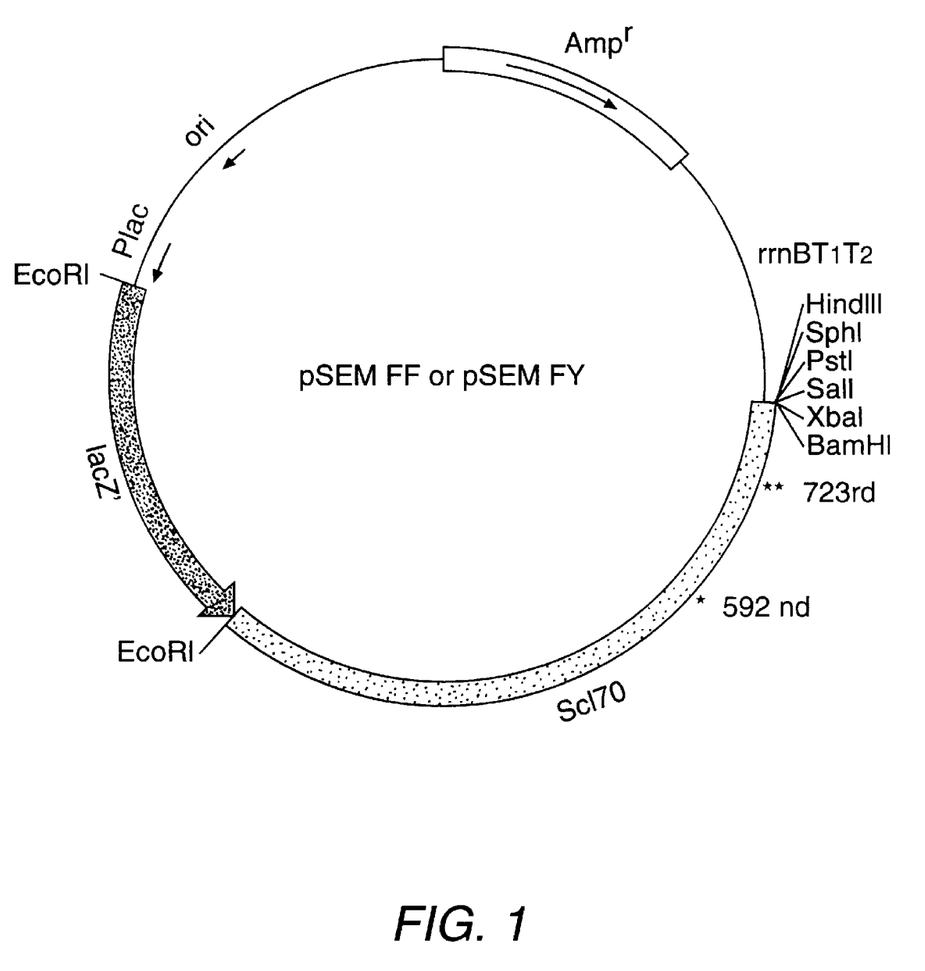
FIG. 1 is a plasmid map of pSEM•FF and pSEM•FY.

After digesting 10 μg of p66FF plasmid with Sac I and EcoRV, the 2.2 kb band containing FF mutant gene was fractionated by electrophoresis with an agarose gel, and recovered by the glass milk method. After digesting 35 μg of an expression vector pSEM with Sac I and Sma I, and the vector DNA was recovered in the same manner. After the fragment having FF mutant gene and the vector as described previously was transfected to XL 1 blue with the ligation mixture. Similarly, an expression experiment was performed using the obtained colony (clone) carrying pSEM•FF. pSEM•FF plasmid map is shown in FIG. 1. As shown clearly in FIG. 1, both the 592nd and the 723rd amino acids of pSEM•FF are Phe.

Example 3

Production of FF mutant by E. coli

1. Expression

Figure 2:
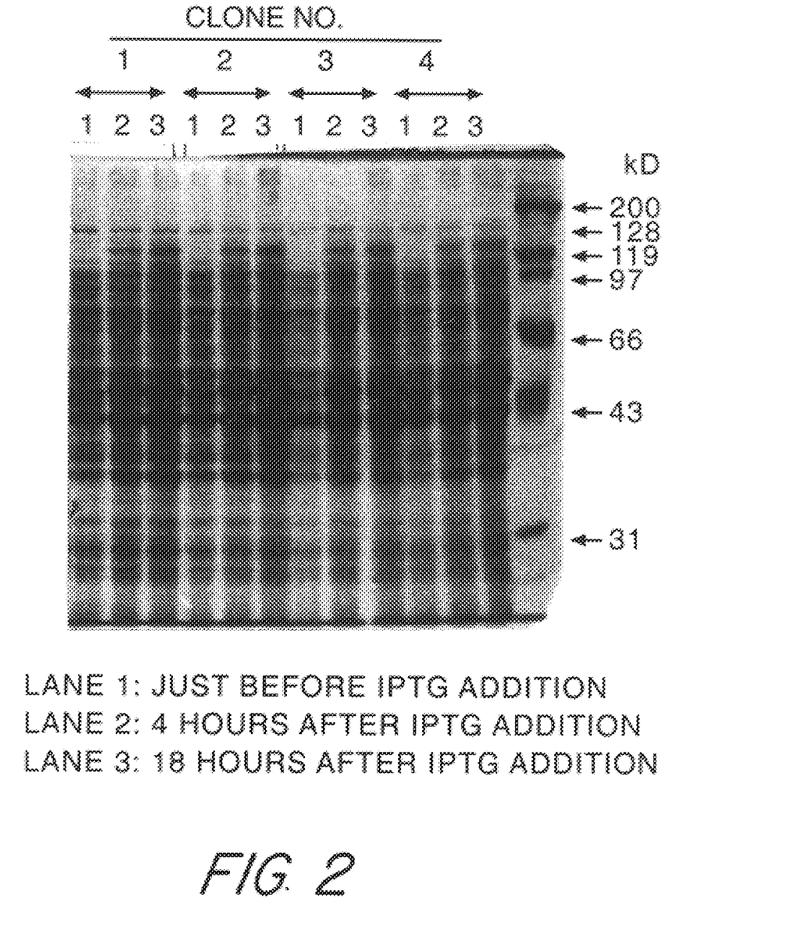
FIG. 2 is a photo of the electrophoresis pattern of the FF mutant produced by E. coli carrying a the FF mutant plasmid.

By using DNA of pSEM•FF, W3110 lac Iq (Hoechst AG) was transformed, and seed clones for an expression experiment were prepared from a single colony. Four independent clones were spread thoroughly on LS plate containing 200 μg/ml ampicillin and stored at 37° C. overnight for cultivation. The bacteria on the plate were collected by a platinum loop, and used to inoculate 3 ml of LS culture medium containing ampicillin, then incubated at 37° C. with shaking for 1.5 hours. Based on the $OD_{550}$ value of the culture, the culture was used to inocutate 20 ml of the culture medium so as to give $OD_{550}$=0.2, and continued to incubate at 37° C. with shaking. After the value of $OD_{550}$ 0.8 was reached in 2 hours, IPTG was added to give a final concentration of 1 mM. 0, 4 and 18 hours after the addition of IPTG, the culture equivalent to $OD_{550}$=1.0 was harvested by centrifugation at 15,000 rpm for 2 minutes, suspended in 50 μl of a sample solution (7M urea, 37.5 mM of Tris-HCl, pH 8.8, 1% of SDS, 12.5% of sucrose, 4% of β-mercaptoethanol, 0.5 mg/ml of bromophenol blue), after boiling for 15 minutes, 7 μl was electrophoresed on a 10% polyacrylamide gel. The electrophoresis pattern of Coomassie staining was shown in FIG. 2. An accumulation of 128 kD band was observed after 4 hours of IPTG addition. The bacterial culture used for purification was performed on a 100 ml scale, cultured for 18 to 20 hours after induction, and harvested by centrifuging for 10 minutes at 6,000 rpm by Hitachi RPR 12-1 rotor.

2. Purification

The bacteria was suspended in 10 ml of TEN buffer (50 mM of Tris, pH 7.5, 10 mM of EDTA, 100 mM NaCl), and each of the mixture 1 ml was distributed into each Eppendorf tube, sonicated for ten times of 2 minutes, centrifuged for 10 minutes at 15,000 rpm, and then the precipitate was obtained. The precipitation was washed with TE buffer (100 mM of Tris-HCl, pH 7.5, 1 mM of EDTA) containing 100 mM. After of n-octylglucopyranoside, the precipitate was suspended in 200 μl of 4M urea, after incubated at 37° C. for 1 hour, centrifuged at 15,000 rpm for 20 minutes, and the resulting precipitate was eluted with 200 μl of 7M urea, and prepared as an antigen protein.

Example 4

Production of Deletion Mutant

For purposes of determining the epitope which anti-Scl-70 antibody recognizes, several kinds of deletion mutants were constructed from the DNA fragment encoding a partial Scl-70 containing Ala at the 96th amino acid through C-terminus of wild-type Scl-70 obtained in Example 1. The construction for each of the expression plasmid was made in accordance with Example 2, and the production of these deletion mutant proteins was made in accordance with Example 3. Shown in FIG. 4 is the se- quence of obtained mutants. The following mutuants were obtained: "EH" containing a partial sequence of Ala at the amino acid through Asp at the 483rd amino acid from EcoRI linker site at the 5' side of wild-type Scl-70 to Hind III (EH mutant hereinafter); "EP" containing a partial sequence of Ala at the 96th amino acid through Lys at the 540th amino acid from EcoRI to PpuMI (EP mutant hereinafter); "ES" containing a partial sequence of Ala at the 96th amino acid through Arg at the 590th amino acid from EcoRI to SnaBI (ES mutant hereinafter); and "SR" containing Thr at the 591st amino acid through Phe at the 765th amino acid from SnaBI to the C-terminus and whose 592nd and 723rd amino acids are replaced with Phe (SR mutant hereinafter).

Example 5

Figure 3:
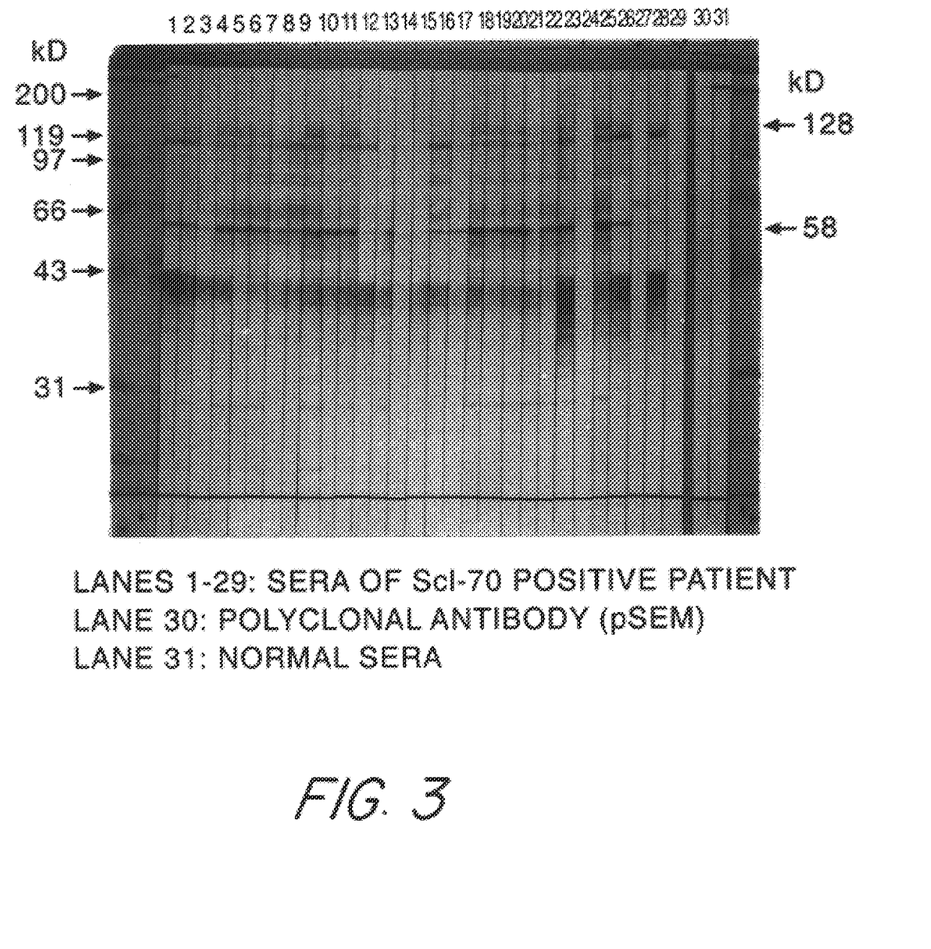
FIG. 3 is a photo of the electrophoresis pattern of the reaction of the FF mutant proteins with anti-Scl-70 antibody in the sera of patient.
Figure 4:
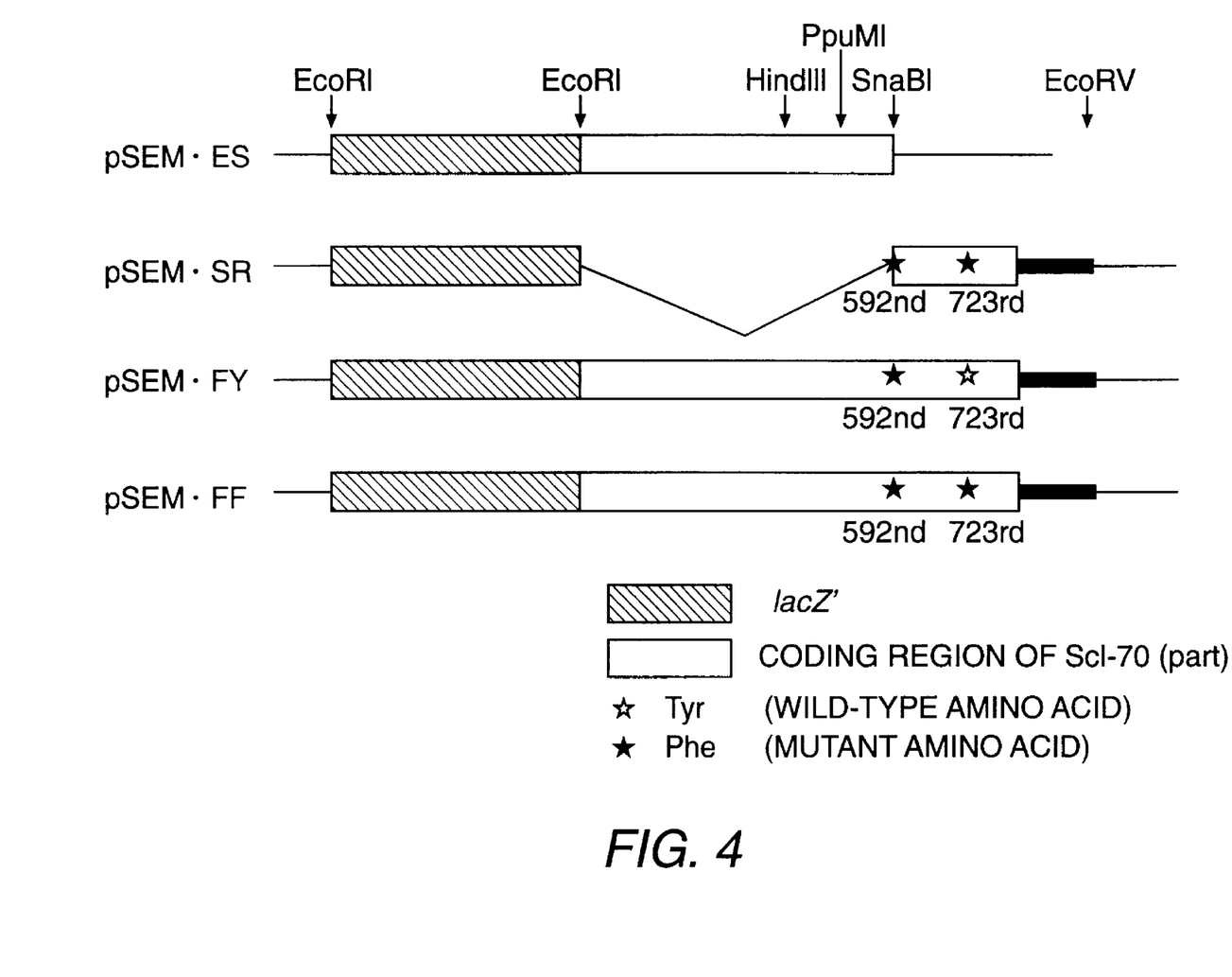
FIG. 4 is a plasmid map encoding Scl-70 protein (FF mutant derived from PSEM•FF, a mutant protein (ES mutant) derived from pSEM•ES and a mutant protein (SR mutant) derived from pSEM•SR.

Measurement of Anti-Scl-70 Antibody in the Sera of Patients Using FF, ES and SR Mutants 1. Western Blotting 7 μl of FF mutant obtained in Example 3 was electrophoresed in a 10% of SDS polyacrylamide gel, and then was transferred to a nitrocellulose filter and blocked with casein buffer (10 mM of Tris-HClr pH 7.5, 150 mM of NaCl, 0.5% of casein) at 4° C. for 1 hour. After hour reacting at room temperature for 1 hour with the patients' sera diluted 100 times with casein buffer containing 200 μg/ml $E.$ $coli$ lysate, washed 4 times with PBS, reacted for 1 hour with rabbit anti-human IgG conjugated with horse radish peroxidase (HRPO), and developed with 4-chloronaphthol. Electrophoresis pattern of the reactant is shown in FIG. 3. 128 kD band and 58 kD band stained with Commassie blue were reacted with the patient's sera. The 58 kD band is considered as a product from the initiation point of transcription.

2. ELISA

Each well of a microtiter plate was coated with 250 ng. of FF mutant obtained in Example 3 and ES and SR mutants obtained in Example 4 at 4° C. overnight, and washed three times with a POD solution (purchased from Behringwerke AG). 50 μl of patients' sera diluted in 100 times with casein buffer containing 200 μg/ml $E.$ $coli$ lysate was added and incubated at 25° C. for 60 minutes. After washing 3 times with the POD solution, anti-human IgG was added to the plate in the same manner as in Example 4-1, and incubated at 25° C. for 60 minutes. Then, TMB (tetramethylbenzidine) was added, and after reacting at 25° C. for 30 minutes, the reaction was stopped by adding 50 μl of 0.5N $H_2SO_4$. The absorbance at $OD_{450}$ was measured. The results are shown in Table 1.

TABLE 1

| Serum No. of patient | ES mutant | FF mutant | SR mutant |
| --- | --- | --- | --- |
| 1 | 1.411 | 1.179 | 0.227 |
| 2 | 1.357 | 1.443 | 0.741 |
| 3 | 1.251 | 0.864 | 0.203 |
| 4 | 0.917 | 1.421 | 1.001 |
| 5 | 0.493 | 1.157 | 0.964 |
| 6 | 0.705 | 1.379 | 1.234 |
| 7 | 0.686 | 1.198 | 1.036 |
| 8 | 1.360 | 0.973 | 0.046 |
| 9 | 0.750 | 1.228 | 0.960 |
| 10 | 0.426 | 0.708 | 0.408 |
| 11 | 2.20 | 2.20 | 0.951 |
| 12 | 0.385 | 1.400 | 1.133 |
| 13 | 0.489 | 0.585 | 0.029 |
| 14 | 0.561 | 1.158 | 0.965 |
| 15 | 0.457 | 0.280 | 0.018 |
| 16 | 0.649 | 1.773 | 0.772 |

The ELISA assay was performed by using ES and FF mutants as antigens, and 2 different groups were found out of 16 specimens; 6 specimens had higher or equivalent values in the ES mutant than in the FF mutant, while 10 specimens had higher absorption in the FF mutant compared to the ES mutant. The specimen group which had higher absorption in the FF mutant compared to ES mutant also has higher reactivity with the SR mutant, suggesting that at least two epitopes existed on ES and SR mutants. Consequently, it is considered that the existence of both epitopes can be firmly recognized when the ES and FF mutants are used as an antigen. It is thought that a difference of clinical feature can be suggested by diagnostic results with both antigens.

Example 6

Analysis of EH and EP Mutants by Western Blotting

Out of the deletion mutants obtained in Example 4, the remaining EH, EP and ES mutants of control as analyzed in Example 5 were analyzed for reactivity with anti-Scl-70 autoantibody by Western Blot analysis using the panel patients' sera. The results were marked as "±" showing extremely weak reaction in EH and EP mutants, respectively, while ES mutant, control used also in Example 5 was marked as "++" showing strong reactivity. These results show that the epitopes which anti-Scl-70 autoantibody recognizes exist between Pro of the 542nd amino acid and the 765th amino acid of C-terminal.

Example 7

Production of Plasmid Coding FY Mutant

After obtaining fragment II in the same manner as in Examples 2 and 3, the fragment was digested with Spl I and Nhe I, the 200 bp fragment was subcloned at Nhe I and SplI sites in vector p66, and plasmid p66FY was obtained. Further, the plasmid was subcloned into pSEM3 at Sac I and Sma I sites in the same manner as in Examples 2 and 4, and pSEM•FY was obtained. Shown in FIG. 1 is the plasmid map of pSEM•FY. As clearly shown in FIG. 1, pSEM•FY has Phe at the 592nd amino acid and Tyr at the 723rd amino acid.

Example 8

Production of FY mutant by $E.$ $coli$

Figure 5:
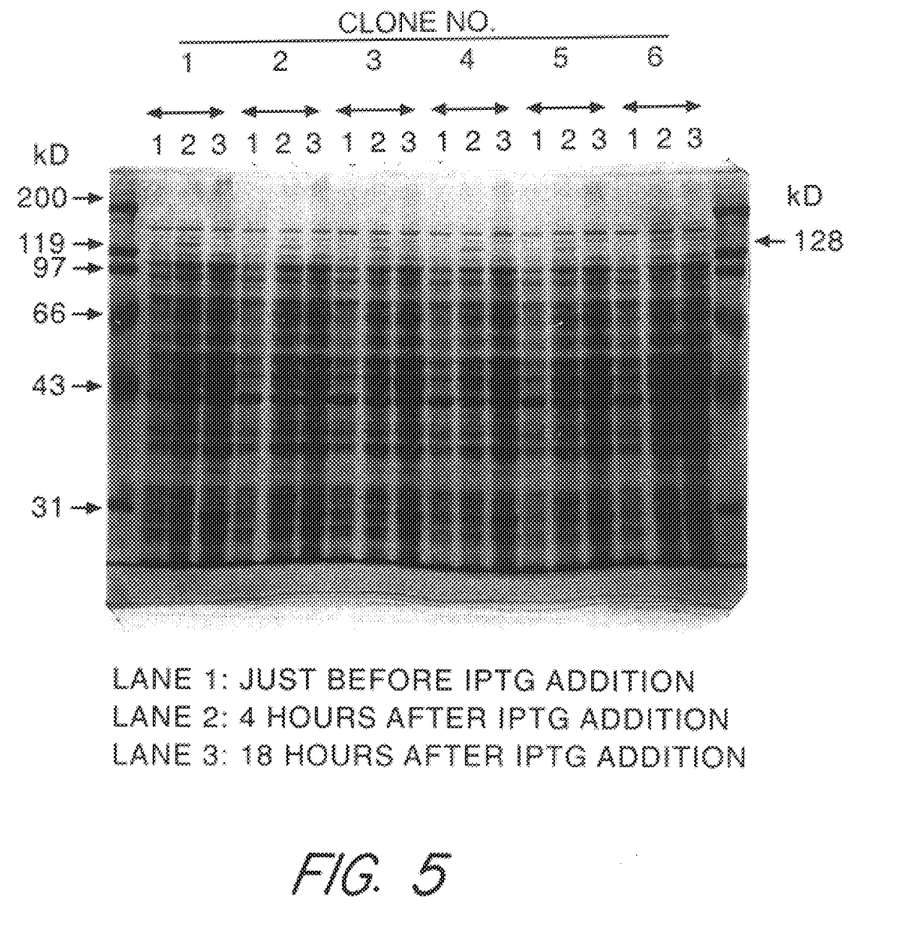
FIG. 5 is a photo of the electrophoresis pattern of the FY mutant produced in E. coli carrying pSEM•FY.

W3110 lacIq strain was transformed with 0.5 ng of pSEM•FY plasmid DNA recovered in XL1 blue, and bacterial lysates were prepared from clones obtained. The clones were spread on LS plate containing 100 μg/ml of ampicillin, and incubated at 37° C. overnight. The bacteria was collected by a platinum loop and pre-cultured in 2 to 3 ml LS culture medium containing ampicillin for 1 to 2 hours. The culture was inoculatd to 15 to 20 ml of the LS culture medium so as to give an $OD_{550}$=0.2, and cultured for 1.5 to 2 hours. IPTG was added to give a final concentration of 1 mM when the $OD_{550}$ reached 0.8 to 1.0, and cultivation was allowed to continue. The cells equivalent to $OD_{550}$=1.0 were harvested at 4 hours and 18 hours after IPTG addition, and a portion of these cells were used for enzyme activity in Example 9. Another portion was used for electrophoresis with polyacrylamide gel and Coomassie staining as in Example 3. A photo of the electrophoresis pattern is shown in FIG. 5. The 128 kD band is observed in 4 hours, however, it has disappeared in 18 hours.

Example 9

Enzyme Activity of FY Mutant

1. Preparation of Supernatant (lysate)

The bacteria equivalent to $OD_{550}$=1.0 is suspended in 300 µl of the sucrose buffer (25% of sucrose, 50 mM of Tris-HCl, pH 8.0, 1 mM of EDTA), washed, and centrifuged at 15,000 rpm for 2 minutes. The precipitate was suspended in 13 µl of the sucrose buffer containing 1 mg/ml lysozyme, and after standing for 2 minutes on ice, the same volume of Brij buffer (10 mM of Tris-HCl, pH 8.0, 0.9% of Brij) was added. After further standing for 2 minutes on ice, 100 mM of KCl was added. And then, after standing for 2 minutes on ice, the supernatant was recovered by centrifugation at 15,000 rpm for 5 minutes.

2. Measurement of Activity

After incubating at 37° C. for 30 minutes, 3 µl of the above supernatant and 200 ng of pUC19 DNA were added in 16 µl of a reaction mixture (50 mM Tris-HCl, pH 8.0, 100 mM KCl, 5 mM DTT, 100 µg/ml BSA). Then 1.5 µg/ml of RNase was added and incubated further for 10 minutes. After incubation, phenol extraction was performed with 8 µl of water saturated phenol and 8 µl of chloroform. 5 µl of loading dye for electrophoresis was added to its supernatant of phenol extraction, incubated at 65° C. for 5 minutes, then electrophoresed in a 0.8% agarose gel. The electrophoresis was performed in TBE buffer (50 mM of Tris-HCl, pH 8.0, 90 mM of boric acid, 1.1 mM of EDTA) at 60V for 3 hours. After electrophoresis, the gel was stained with 0.5 µg/ml of ethidium bromide. A photo of the electrophoresis pattern is shown in FIG. 6.

Figure 6:
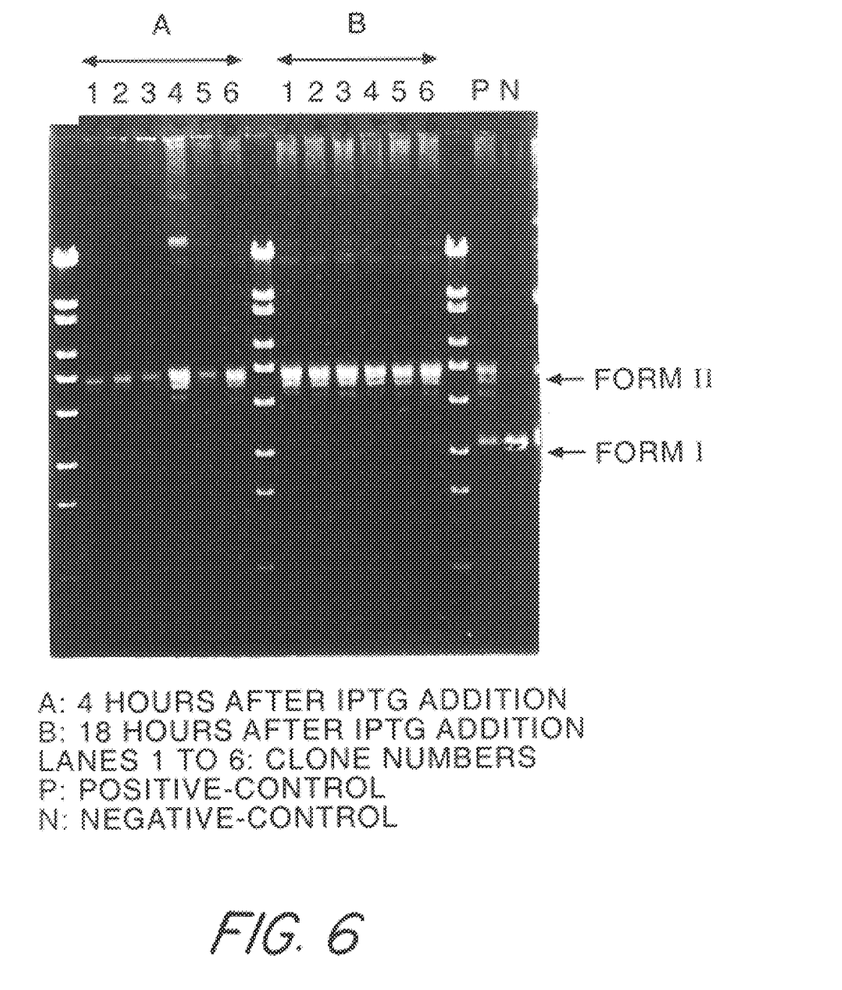
FIG. 6 is a photo of the electrophoresis pattern of the FY mutant.

FIG. 6 shows the result of enzyme activity of the samples at 4 hours and 18 hours after IPTG addition of 6 clones harvested in Example 8. In each lane, pUC19 moves from twisted form I to open circle form II, and thus topoisomerase activity was recognized. These results suggests a possibility of producing recombinant human topoisomerase I in *E. coli* carrying PSEM•FY mutant proteins.

SEQ ID No.:1 of the Sequence Listing shows an amino acid sequence and the corresponding DNA sequence encoding a mutant protein in which both tyrosine at the 592nd and 723rd amino acid positions of human DNA topoisomerase I are replaced with phenylalanine The preferable mutant proteins in the present invention shall be more illustratively explained on the basis of the above-mentioned Sequence Listing.

1. A mutant protein (ES mutant) of human DNA topoisomerase I having an amino acid sequence from the 96th to the 590th amino acid in SEQ ID No.:1 of the Sequence Listing.
2. A mutant protein (SR mutant) of human DNA topoisomerase I having an amino acid sequence from the 591st to the 765th amino acid in SEQ ID No.:1 of the Sequence Listing.
3. A mutant protein of human DNA topoisomerase I having an amino acid sequence from the 591st to the 765th amino acid in SEQ ID No.:1 of the Sequence Listing and being replaced with tyrosine at the 723rd amino acid position.
4. A mutant protein (FF mutant) of human DNA topoisomerase I having an amino acid sequence from the 96th to the 765th amino acid in SEQ ID No.:1 of the Sequence Listing.
5. A mutant protein (FY mutant)of human DNA topoisomerase I having an amino acid sequence from the 96th to the 765th amino acid in SEQ ID No.:1 of the Sequence Listing and being replaced with tyrosine at the 723rd amino acid position.
6. A mutant protein of human DNA topoisomerase I having an amino acid sequence from the 542nd to the 765th amino acid in SEQ ID No.:1 of the Sequence Listing.
7. A mutant protein of human DNA topoisomerase I having an amino acid sequence from the 542nd to the 765th amino acid in SEQ ID No.:1 of the Sequence Listing and being replaced with tyrosine at the 723rd amino acid position.
8. A mutant protein of human DNA topoisomerase I having an amino acid sequence from the 1st to the 765th amino acid in SEQ ID No.:1 of the Sequence Listing.
9. A mutant protein of human DNA topoisomerase I having an amino acid sequence from the 1st to the 765th amino acid in SEQ ID No.:1 of the Sequence Listing and being replaced with tyrosine at the 723rd amino acid position.
10. A mutant protein of human DNA topoisomerase I having an amino acid sequence from the 1st to the 765th amino acid in SEQ ID No.:1 of the Sequence Listing, in which the amino acids at the 592nd position and 723rd amino acid position are both lacking.
11. A mutant protein of human DNA topoisomerase I having an amino acid sequence from the 1st to the 765th amino acid in SEQ ID No.:1 of the Sequence Listing, in which one of the amino acids at the 592nd amino acid position and 723rd amino acid position is lacking and the other is replaced with tyrosine. The above-mentioned mutant proteins shall be utilized for the detecting autoantibodies.

Utilized possibility in industry

The mutant protein (FF mutant) of human DNA topoisomerase I provided by the present invention shall be utilized as a detection agent for autoimmune diseases. The mutant protein (FY mutant) of human DNA topoisomerase I, in the same way, shall be utilized for the production of recombinant human topoisomerase.

What is claimed is:

1. A mutant human DNA topoisomerase I protein comprising the amino acid sequence from the 96th through the 590th of the amino acid sequence described in SEQ ID No.:1.

2. A mutant of human DNA topoisomerase I protein comprising the amino acid sequence from the 591st through the 765th of the amino acid sequence described in SEQ ID No.:1.

3. A mutant human DNA topoisomerase I protein as claimed in claim 2 wherein the amino acid at the 723rd position is tyrosine.

4. A mutant human DNA topoisomerase I protein comprising the amino acid sequence from the 96th through the 765th of the amino acid sequence described in SEQ ID No.:1.

5. A mutant human DNA topoisomerase I protein as claimed in claim 4 wherein the amino acid at the 723rd position is tyrosine.

6. A mutant human DNA topoisomerase I protein comprising the amino acid sequence from the 542nd through the 765th of the amino acid sequence described in SEQ ID No.:1.

7. A mutant human DNA topoisomerase I protein as claimed in claim 6 wherein the amino acid at the 723rd position is tyrosine.

8. A mutant human DNA topoisomerase I protein comprising the amino acid sequence from the 1st through the 765th of the amino acid sequence described in SEQ ID No.:1.

9. A mutant human DNA topoisomerase I protein as claimed in claim 8 wherein the amino acid at the 723rd position is tyrosine.

10. A mutant human DNA topoisomerase I protein comprising the amino acid sequence from the 1st through the 765th of the amino acid sequence described in SEQ ID No.:1, in which the amino acids at the 592nd position and 723rd position are both lacking.

11. A method of detecting an autoantibody comprising:
a) contacting the protein as claimed in any one of claims 1 2, 4, 6, 8, and 10 with sera from a patient; and
b) measuring the autoantibody in an immunoassay.

12. A method of detecting an autoantibody comprising:
a) contacting the protein as claimed in claim 3 with sera from a patient; and
b) measuring the autoantibody in an immunoassay.

13. A method of detecting an autoantibody comprising:
a) contacting the protein as claimed in claim 5 with sera from a patient; and
b) measuring the autoantibody in an immunoassay.

14. A method of detecting an autoantibody comprising:
a) contacting the protein as claimed in claim 7 with sera from a patient; and
b) measuring the autoantibody in an immunoassay.

15. A method of detecting an autoantibody comprising:
a) contacting the protein as claimed in claim 9 with sera from a patient; and
b) measuring the autoantibody in an immunoassay.

16. A mutant human DNA topoisomerase I protein comprising an amino acid sequence from the 542nd amino acid through the 592nd amino acid of the amino acid sequence described in SEQ ID NO:1.

17. A mutant human topoisomerase I protein comprising an amino acid sequence from the 542nd amino acid through the 592nd amino acid of the amino acid sequence described in SEQ ID NO: 1, wherein the amino acid at the 592nd position is lacking.

18. A mutant human DNA topoisomerase I protein comprising an amino acid sequence from the 1st through the 765th amino acid of the amino acid sequence described in SEQ ID NO:1, in which one amino acid at the 592nd position is lacking and the amino acid at the 723rd position is replaced with tyrosine.

19. A method of detecting an autoantibody comprising:
a) contacting the protein as claimed in any one of claims 16, 17, and 18 with sera from a patient; and
b) measuring the autoantibody in an immunoassay.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 3645 base pairs
        ( B ) TYPE: nucleic acid
        ( C ) STRANDEDNESS: double
        ( D ) TOPOLOGY: linear     ( i i ) MOLECULE TYPE: cDNA to mRNA ( i x ) FEATURE:
    ( A ) NAME/KEY: CDS
    ( B ) LOCATION: 212..2506
    ( D ) OTHER INFORMATION: /label=FFmutant ( x i ) SEQUENCE DESCRIPTION: SEQ ID NO:1:

```
GAATTCGGGC  GCCGCCCGCC  CGGCAGTCAG  GCAGCGTCGC  CGCCGTGGTA  GCAGCCTCAG           60

CCGTTTCTGG  AGTCTCGGGC  CCACAGTCAC  CGCCGCTTAC  CTGCGCCTCC  TCGAGCCTCC          120

GGAGTCCCCG  TCCGCCCGCA  CAGGCCGGTT  CGCCGTCTGC  GTCTCCCCCA  CGCCGCCTCG          180

CCTGCCGCCG  CGCTCGTCCC  TCCGGGCCGA  C ATG AGT GGG GAC CAC CTC CAC               232
                                     Met Ser Gly Asp His Leu His
                                      1               5

AAC GAT TCC CAG ATC GAA GCG GAT TTC CGA TTG AAT GAT TCT CAT AAA                 280
Asn Asp Ser Gln Ile Glu Ala Asp Phe Arg Leu Asn Asp Ser His Lys
             10              15                  20

CAC AAA GAT AAA CAC AAA GAT CGA GAA CAC CGG CAC AAA GAA CAC AAG                 328
His Lys Asp Lys His Lys Asp Arg Glu His Arg His Lys Glu His Lys
         25              30                  35

AAG GAG AAG GAC CGG GAA AAG TCC AAG CAT AGC AAC AGT GAA CAT AAA                 376
Lys Glu Lys Asp Arg Glu Lys Ser Lys His Ser Asn Ser Glu His Lys
 40              45                  50                      55

GAT TCT GAA AAG AAA CAC AAA GAG AAG GAG AAG ACC AAA CAC AAA GAT                 424
Asp Ser Glu Lys Lys His Lys Glu Lys Glu Lys Thr Lys His Lys Asp
                     60                  65                  70

GGA AGC TCA GAA AAG CAT AAA GAC AAA CAT AAA GAC AGA GAC AAG GAA                 472
Gly Ser Ser Glu Lys His Lys Asp Lys His Lys Asp Arg Asp Lys Glu
                 75              80                  85

AAA CGA AAA GAG GAA AAG GTT CGA GCC TCT GGG GAT GCA AAA ATA AAG                 520
Lys Arg Lys Glu Glu Lys Val Arg Ala Ser Gly Asp Ala Lys Ile Lys
         90              95                 100

AAG GAG AAG GAA AAT GGC TTC TCT AGT CCA CCA CAA ATT AAA GAT GAA                 568
Lys Glu Lys Glu Asn Gly Phe Ser Ser Pro Pro Gln Ile Lys Asp Glu
    105                 110                 115

CCT GAA GAT GAT GGC TAT TTT GTT CCT CCT AAA GAG GAT ATA AAG CCA                 616
Pro Glu Asp Asp Gly Tyr Phe Val Pro Pro Lys Glu Asp Ile Lys Pro
120                 125                 130                 135

TTA AAG AGA CCT CGA GAT GAG GAT GAT GTT GAT TAT AAA CCT AAG AAA                 664
Leu Lys Arg Pro Arg Asp Glu Asp Asp Val Asp Tyr Lys Pro Lys Lys
                140                 145                 150

ATT AAA ACA GAA GAT ACC AAG AAG GAG AAG AAA AGA AAA CTA GAA GAA                 712
Ile Lys Thr Glu Asp Thr Lys Lys Glu Lys Lys Arg Lys Leu Glu Glu
                155                 160                 165

GAA GAG GAT GGT AAA TTG AAA AAA CCC AAG AAT AAA GAT AAA GAT AAA                 760
Glu Glu Asp Gly Lys Leu Lys Lys Pro Lys Asn Lys Asp Lys Asp Lys
            170                 175                 180

AAA GTT CCT GAG CCA GAT AAC AAG AAA AAG AAG CCG AAG AAA GAA GAG                 808
Lys Val Pro Glu Pro Asp Asn Lys Lys Lys Lys Pro Lys Lys Glu Glu
185                 190                 195

GAA CAG AAG TGG AAA TGG TGG GAA GAA GAG CGC TAT CCT GAA GGC ATC                 856
Glu Gln Lys Trp Lys Trp Trp Glu Glu Glu Arg Tyr Pro Glu Gly Ile
200                 205                 210                 215

AAG TGG AAA TTC CTA GAA CAT AAA GGT CCA GTA TTT GCC CCA CCA TAT                 904
Lys Trp Lys Phe Leu Glu His Lys Gly Pro Val Phe Ala Pro Pro Tyr
                220                 225                 230

GAG CCT CTT CCA GAG AAT GTC AAG TTT TAT TAT GAT GGT AAA GTC ATG                 952
Glu Pro Leu Pro Glu Asn Val Lys Phe Tyr Tyr Asp Gly Lys Val Met
                235                 240                 245

AAG CTG AGC CCC AAA GCA GAG GAA GTA GCT ACG TTC TTT GCA AAA ATG                1000
Lys Leu Ser Pro Lys Ala Glu Glu Val Ala Thr Phe Phe Ala Lys Met
```

-continued

|     | 250 |     |     |     | 255 |     |     |     | 260 |     |     |     |     |     |     |      |
|-----|-----|-----|-----|-----|-----|-----|-----|-----|-----|-----|-----|-----|-----|-----|-----|------|
| CTC | GAC | CAT | GAA | TAT | ACT | ACC | AAG | GAA | ATA | TTT | AGG | AAA | AAT | TTC | TTT | 1048 |
| Leu | Asp | His | Glu | Tyr | Thr | Thr | Lys | Glu | Ile | Phe | Arg | Lys | Asn | Phe | Phe |      |
| 265 |     |     |     |     | 270 |     |     |     |     | 275 |     |     |     |     |     |      |

| AAA | GAC | TGG | AGA | AAG | GAA | ATG | ACT | AAT | GAA | GAG | AAG | AAT | ATT | ATC | ACC | 1096 |
|-----|-----|-----|-----|-----|-----|-----|-----|-----|-----|-----|-----|-----|-----|-----|-----|------|
| Lys | Asp | Trp | Arg | Lys | Glu | Met | Thr | Asn | Glu | Glu | Lys | Asn | Ile | Ile | Thr |      |
| 280 |     |     |     |     | 285 |     |     |     |     | 290 |     |     |     |     | 295 |      |

| AAC | CTA | AGC | AAA | TGT | GAT | TTT | ACC | CAG | ATG | AGC | CAG | TAT | TTC | AAA | GCC | 1144 |
|-----|-----|-----|-----|-----|-----|-----|-----|-----|-----|-----|-----|-----|-----|-----|-----|------|
| Asn | Leu | Ser | Lys | Cys | Asp | Phe | Thr | Gln | Met | Ser | Gln | Tyr | Phe | Lys | Ala |      |
|     |     |     |     | 300 |     |     |     |     | 305 |     |     |     |     | 310 |     |      |

| CAG | ACG | GAA | GCT | CGG | AAA | CAG | ATG | AGC | AAG | GAA | GAG | AAA | CTG | AAA | ATC | 1192 |
|-----|-----|-----|-----|-----|-----|-----|-----|-----|-----|-----|-----|-----|-----|-----|-----|------|
| Gln | Thr | Glu | Ala | Arg | Lys | Gln | Met | Ser | Lys | Glu | Glu | Lys | Leu | Lys | Ile |      |
|     |     |     | 315 |     |     |     |     | 320 |     |     |     |     | 325 |     |     |      |

| AAA | GAG | GAG | AAT | GAA | AAA | TTA | CTG | AAA | GAA | TAT | GGA | TTC | TGT | ATT | ATG | 1240 |
|-----|-----|-----|-----|-----|-----|-----|-----|-----|-----|-----|-----|-----|-----|-----|-----|------|
| Lys | Glu | Glu | Asn | Glu | Lys | Leu | Leu | Lys | Glu | Tyr | Gly | Phe | Cys | Ile | Met |      |
|     |     | 330 |     |     |     |     | 335 |     |     |     |     | 340 |     |     |     |      |

| GAT | AAC | CAC | AAA | GAG | AGG | ATT | GCT | AAC | TTC | AAG | ATA | GAG | CCT | CCT | GGA | 1288 |
|-----|-----|-----|-----|-----|-----|-----|-----|-----|-----|-----|-----|-----|-----|-----|-----|------|
| Asp | Asn | His | Lys | Glu | Arg | Ile | Ala | Asn | Phe | Lys | Ile | Glu | Pro | Pro | Gly |      |
| 345 |     |     |     |     | 350 |     |     |     |     | 355 |     |     |     |     |     |      |

| CTT | TTC | CGT | GGC | CGC | GGC | AAC | CAC | CCC | AAG | ATG | GGC | ATG | CTG | AAG | AGA | 1336 |
|-----|-----|-----|-----|-----|-----|-----|-----|-----|-----|-----|-----|-----|-----|-----|-----|------|
| Leu | Phe | Arg | Gly | Arg | Gly | Asn | His | Pro | Lys | Met | Gly | Met | Leu | Lys | Arg |      |
| 360 |     |     |     |     | 365 |     |     |     |     | 370 |     |     |     |     | 375 |      |

| CGA | ATC | ATG | CCC | GAG | GAT | ATA | ATC | ATC | AAC | TGT | AGC | AAA | GAT | GCC | AAG | 1384 |
|-----|-----|-----|-----|-----|-----|-----|-----|-----|-----|-----|-----|-----|-----|-----|-----|------|
| Arg | Ile | Met | Pro | Glu | Asp | Ile | Ile | Ile | Asn | Cys | Ser | Lys | Asp | Ala | Lys |      |
|     |     |     |     | 380 |     |     |     |     | 385 |     |     |     |     | 390 |     |      |

| GTT | CCT | TCT | CCT | CCT | CCA | GGA | CAT | AAG | TGG | AAA | GAA | GTC | CGG | CAT | GAT | 1432 |
|-----|-----|-----|-----|-----|-----|-----|-----|-----|-----|-----|-----|-----|-----|-----|-----|------|
| Val | Pro | Ser | Pro | Pro | Pro | Gly | His | Lys | Trp | Lys | Glu | Val | Arg | His | Asp |      |
|     |     |     | 395 |     |     |     |     | 400 |     |     |     |     | 405 |     |     |      |

| AAC | AAG | GTT | ACT | TGG | CTG | GTT | TCC | TGG | ACA | GAG | AAC | ATC | CAA | GGT | TCC | 1480 |
|-----|-----|-----|-----|-----|-----|-----|-----|-----|-----|-----|-----|-----|-----|-----|-----|------|
| Asn | Lys | Val | Thr | Trp | Leu | Val | Ser | Trp | Thr | Glu | Asn | Ile | Gln | Gly | Ser |      |
|     |     |     | 410 |     |     |     |     | 415 |     |     |     |     | 420 |     |     |      |

| ATT | AAA | TAC | ATC | ATG | CTT | AAC | CCT | AGT | TCA | CGA | ATC | AAG | GGT | GAG | AAG | 1528 |
|-----|-----|-----|-----|-----|-----|-----|-----|-----|-----|-----|-----|-----|-----|-----|-----|------|
| Ile | Lys | Tyr | Ile | Met | Leu | Asn | Pro | Ser | Ser | Arg | Ile | Lys | Gly | Glu | Lys |      |
|     | 425 |     |     |     |     | 430 |     |     |     |     | 435 |     |     |     |     |      |

| GAC | TGG | CAG | AAA | TAC | GAG | ACT | GCT | CGG | CGG | CTG | AAA | AAA | TGT | GTG | GAC | 1576 |
|-----|-----|-----|-----|-----|-----|-----|-----|-----|-----|-----|-----|-----|-----|-----|-----|------|
| Asp | Trp | Gln | Lys | Tyr | Glu | Thr | Ala | Arg | Arg | Leu | Lys | Lys | Cys | Val | Asp |      |
| 440 |     |     |     |     | 445 |     |     |     |     | 450 |     |     |     |     | 455 |      |

| AAG | ATC | CGG | AAC | CAG | TAT | CGA | GAA | GAC | TGG | AAG | TCC | AAA | GAG | ATG | AAA | 1624 |
|-----|-----|-----|-----|-----|-----|-----|-----|-----|-----|-----|-----|-----|-----|-----|-----|------|
| Lys | Ile | Arg | Asn | Gln | Tyr | Arg | Glu | Asp | Trp | Lys | Ser | Lys | Glu | Met | Lys |      |
|     |     |     |     | 460 |     |     |     |     | 465 |     |     |     |     | 470 |     |      |

| GTC | CGG | CAG | AGA | GCT | GTA | GCC | CTG | TAC | TTC | ATC | GAC | AAG | CTT | GCT | CTG | 1672 |
|-----|-----|-----|-----|-----|-----|-----|-----|-----|-----|-----|-----|-----|-----|-----|-----|------|
| Val | Arg | Gln | Arg | Ala | Val | Ala | Leu | Tyr | Phe | Ile | Asp | Lys | Leu | Ala | Leu |      |
|     |     |     | 475 |     |     |     |     | 480 |     |     |     |     | 485 |     |     |      |

| AGA | GCA | GGC | AAT | GAA | AAG | GAG | GAA | GGA | GAA | ACA | GCG | GAC | ACT | GTG | GGC | 1720 |
|-----|-----|-----|-----|-----|-----|-----|-----|-----|-----|-----|-----|-----|-----|-----|-----|------|
| Arg | Ala | Gly | Asn | Glu | Lys | Glu | Glu | Gly | Glu | Thr | Ala | Asp | Thr | Val | Gly |      |
|     |     |     | 490 |     |     |     |     | 495 |     |     |     |     | 500 |     |     |      |

| TGC | TGC | TCA | CTT | CGT | GTG | GAG | CAC | ATC | AAT | CTA | CAC | CCA | GAG | TTG | GAT | 1768 |
|-----|-----|-----|-----|-----|-----|-----|-----|-----|-----|-----|-----|-----|-----|-----|-----|------|
| Cys | Cys | Ser | Leu | Arg | Val | Glu | His | Ile | Asn | Leu | His | Pro | Glu | Leu | Asp |      |
|     | 505 |     |     |     |     | 510 |     |     |     |     | 515 |     |     |     |     |      |

| GGT | CAG | GAA | TAT | GTG | GTA | GAG | TTT | GAC | TTC | CTC | GGG | AAG | GAC | TCC | ATC | 1816 |
|-----|-----|-----|-----|-----|-----|-----|-----|-----|-----|-----|-----|-----|-----|-----|-----|------|
| Gly | Gln | Glu | Tyr | Val | Val | Glu | Phe | Asp | Phe | Leu | Gly | Lys | Asp | Ser | Ile |      |
| 520 |     |     |     |     | 525 |     |     |     |     | 530 |     |     |     |     | 535 |      |

| AGA | TAC | TAT | AAC | AAG | GTC | CCT | GTT | GAG | AAA | CGA | GTT | TTT | AAG | AAC | CTA | 1864 |
|-----|-----|-----|-----|-----|-----|-----|-----|-----|-----|-----|-----|-----|-----|-----|-----|------|
| Arg | Tyr | Tyr | Asn | Lys | Val | Pro | Val | Glu | Lys | Arg | Val | Phe | Lys | Asn | Leu |      |
|     |     |     |     | 540 |     |     |     |     | 545 |     |     |     |     | 550 |     |      |

| CAA | CTA | TTT | ATG | GAG | AAC | AAG | CAG | CCC | GAG | GAT | GAT | CTT | TTT | GAT | AGA | 1912 |
|-----|-----|-----|-----|-----|-----|-----|-----|-----|-----|-----|-----|-----|-----|-----|-----|------|
| Gln | Leu | Phe | Met | Glu | Asn | Lys | Gln | Pro | Glu | Asp | Asp | Leu | Phe | Asp | Arg |      |
|     |     |     | 555 |     |     |     |     | 560 |     |     |     |     | 565 |     |     |      |

| CTC | AAT | ACT | GGT | ATT | CTG | AAT | AAG | CAT | CTT | CAG | GAT | CTC | ATG | GAG | GGC | 1960 |
|-----|-----|-----|-----|-----|-----|-----|-----|-----|-----|-----|-----|-----|-----|-----|-----|------|
| Leu | Asn | Thr | Gly | Ile | Leu | Asn | Lys | His | Leu | Gln | Asp | Leu | Met | Glu | Gly |      |

-continued

```
             570                      575                      580
TTG ACA GCC AAG GTA TTC CGT ACG TTC AAT GCC TCC ATC ACG CTA CAG         2008
Leu Thr Ala Lys Val Phe Arg Thr Phe Asn Ala Ser Ile Thr Leu Gln
    585                 590                 595

CAG CAG CTA AAA GAA CTG ACA GCC CCG GAT GAG AAC ATC CCA GCG AAG         2056
Gln Gln Leu Lys Glu Leu Thr Ala Pro Asp Glu Asn Ile Pro Ala Lys
600                 605                 610                     615

ATC CTT TCT TAT AAC CGT GCC AAT CGA GCT GTT GCA ATT CTT TGT AAC         2104
Ile Leu Ser Tyr Asn Arg Ala Asn Arg Ala Val Ala Ile Leu Cys Asn
                620                 625                 630

CAT CAG AGG GCA CCA CCA AAA ACT TTT GAG AAG TCT ATG ATG AAC TTG         2152
His Gln Arg Ala Pro Pro Lys Thr Phe Glu Lys Ser Met Met Asn Leu
            635                 640                 645

CAA ACT AAG ATT GAT GCC AAG AAG GAA CAG CTA GCA GAT GCC CGG AGA         2200
Gln Thr Lys Ile Asp Ala Lys Lys Glu Gln Leu Ala Asp Ala Arg Arg
        650                 655                 660

GAC CTG AAA AGT GCT AAG GCT GAT GCC AAG GTC ATG AAG GAT GCA AAG         2248
Asp Leu Lys Ser Ala Lys Ala Asp Ala Lys Val Met Lys Asp Ala Lys
665                 670                 675

ACG AAG AAG GTA GTA GAG TCA AAG AAG AAG GCT GTT CAG AGA CTG GAG         2296
Thr Lys Lys Val Val Glu Ser Lys Lys Lys Ala Val Gln Arg Leu Glu
680                 685                 690                     695

GAA CAG TTG ATG AAG CTG GAA GTT CAA GCC ACA GAC CGA GAG GAA AAT         2344
Glu Gln Leu Met Lys Leu Glu Val Gln Ala Thr Asp Arg Glu Glu Asn
                700                 705                 710

AAA CAG ATT GCC CTG GGA ACC TCC AAA CTC AAT TTT CTG GAC CCT AGG         2392
Lys Gln Ile Ala Leu Gly Thr Ser Lys Leu Asn Phe Leu Asp Pro Arg
            715                 720                 725

ATC ACA GTG GCT TGG TGC AAG AAG TGG GGT GTC CCA ATT GAG AAG ATT         2440
Ile Thr Val Ala Trp Cys Lys Lys Trp Gly Val Pro Ile Glu Lys Ile
        730                 735                 740

TAC AAC AAA ACC CAG CGG GAG AAG TTT GCC TGG GCC ATT GAC ATG GCT         2488
Tyr Asn Lys Thr Gln Arg Glu Lys Phe Ala Trp Ala Ile Asp Met Ala
745                 750                 755

GAT GAA GAC TAT GAG TTT TAGCCAGTCT CAAGAGGCAG AGTTCTGTGA                2536
Asp Glu Asp Tyr Glu Phe
760                 765

AGAGGAACAG TGTGGTTTGG GAAAGATGGA TAAACTGAGC CTCACTTGCC CTCGTGCCTG       2596

GGGGAGAGAG GCAGCAAGTC TTAACAAACC AACATCTTTG CGAAAAGATA AACCTGGAGA       2656

TATTATAAGG GAGAGCTGAG CCAGTTGTCC TATGGACAAC TTATTTAAAA ATATTTCAGA       2716

TATCAAAATT CTAGCTGTAT GATTTGTTTT GAATTTTGTT TTTATTTTCA AGAGGGCAAG       2776

TGGATGGGAA TTTGTCAGCG TTCTACCAGG CAAATTCACT GTTTCACTGA AATGTTTGGA       2836

TTCTCTTAGC TACTGTATGC AAAGTCCGAT TATATTGGTG CGTTTTTACA GTTAGGGTTT       2896

TGCAATAACT TCTATATTTT AATAGAAATA AATTCCTAAA CTCCCTTCCC TCTCTCCCAT       2956

TTCAGGAATT TAAAATTAAG TAGAACAAAA AACCCAGCGC ACCTGTTAGA GTCGTCACTC       3016

TCTATTGTCA TGGGGATCAA TTTTCATTAA ACTTGAAGCA GTCGTGGCTT TGGCAGTGTT       3076

TTGGTTCAGA CACCTGTTCA CAGAAAAAGC ATGATGGGAA AATATTTCCT GACTTGAGTG       3136

TTCCTTTTTA AATGTGAATT TTTTTTTTTT TTAATTATTT TAAAATATTT AAACCTTTTT       3196

CTTGATCTTA AAGATCGTGT AGATTGGGGT TGGGGAGGGA TGAAGGGCGA GTGAATCTAA       3256

GGATAATGAA ATAATCAGTG ACTGAAACCA TTTTCCCATC ATCCTTTGTT CTGAGCATTC       3316

GCTGTACCCT TTAAGATATC CATCTTTTTC TTTTTAACCC TAATCTTTCA CTTGAAAGAT       3376

TTTATTGTAT AAAAAGTTTC ACAGGTCAAT AAACTTAGAG GAAAATGAGT ATTTGGTCCA       3436
```

```
AAAAAGGAA    AAATAATCAA    GATTTTAGGG    CTTTTATTTT    TTCTTTTGTA    ATTGTGTAAA        3496

AAATGGAAAA   AAACATAAAA    AGCAGAATTT    TAATGTGAAG    ACATTTTTG     CTATAATCAT        3556

TAGTTTTAGA   GGCATTGTTA    GTTAGTGTG     TGTGCAGAGT    CCATTTCCCA    CATCTTTCCT        3616

CAAGTATCTT   CTATTTTTAT    CATGAATTC                                                   3645
```

(2) INFORMATION FOR SEQ ID NO:2:

(i) SEQUENCE CHARACTERISTICS:
        (A) LENGTH: 765 amino acids
        (B) TYPE: amino acid
        (D) TOPOLOGY: linear     (ii) MOLECULE TYPE: protein     (xi) SEQUENCE DESCRIPTION: SEQ ID NO:2:

```
Met  Ser  Gly  Asp  His  Leu  His  Asn  Asp  Ser  Gln  Ile  Glu  Ala  Asp  Phe
 1              5                        10                       15

Arg  Leu  Asn  Asp  Ser  His  Lys  His  Lys  Asp  Lys  His  Lys  Asp  Arg  Glu
              20                       25                       30

His  Arg  His  Lys  Glu  His  Lys  Lys  Glu  Lys  Asp  Arg  Glu  Lys  Ser  Lys
              35                       40                       45

His  Ser  Asn  Ser  Glu  His  Lys  Asp  Ser  Glu  Lys  Lys  His  Lys  Glu  Lys
 50                       55                       60

Glu  Lys  Thr  Lys  His  Lys  Asp  Gly  Ser  Ser  Glu  Lys  His  Lys  Asp  Lys
 65                       70                       75                       80

His  Lys  Asp  Arg  Asp  Lys  Glu  Lys  Arg  Lys  Glu  Glu  Lys  Val  Arg  Ala
                   85                       90                       95

Ser  Gly  Asp  Ala  Lys  Ile  Lys  Lys  Glu  Lys  Glu  Asn  Gly  Phe  Ser  Ser
                  100                      105                      110

Pro  Pro  Gln  Ile  Lys  Asp  Glu  Pro  Glu  Asp  Asp  Gly  Tyr  Phe  Val  Pro
                  115                      120                      125

Pro  Lys  Glu  Asp  Ile  Lys  Pro  Leu  Lys  Arg  Pro  Arg  Asp  Glu  Asp  Asp
              130                      135                      140

Val  Asp  Tyr  Lys  Pro  Lys  Lys  Ile  Lys  Thr  Glu  Asp  Thr  Lys  Lys  Glu
145                      150                      155                      160

Lys  Lys  Arg  Lys  Leu  Glu  Glu  Glu  Glu  Asp  Gly  Lys  Leu  Lys  Lys  Pro
                  165                      170                      175

Lys  Asn  Lys  Asp  Lys  Asp  Lys  Lys  Val  Pro  Glu  Pro  Asp  Asn  Lys  Lys
                  180                      185                      190

Lys  Lys  Pro  Lys  Lys  Glu  Glu  Glu  Gln  Lys  Trp  Lys  Trp  Trp  Glu  Glu
              195                      200                      205

Glu  Arg  Tyr  Pro  Glu  Gly  Ile  Lys  Trp  Lys  Phe  Leu  Glu  His  Lys  Gly
     210                      215                      220

Pro  Val  Phe  Ala  Pro  Pro  Tyr  Glu  Pro  Leu  Pro  Glu  Asn  Val  Lys  Phe
225                      230                      235                      240

Tyr  Tyr  Asp  Gly  Lys  Val  Met  Lys  Leu  Ser  Pro  Lys  Ala  Glu  Glu  Val
                  245                      250                      255

Ala  Thr  Phe  Phe  Ala  Lys  Met  Leu  Asp  His  Glu  Tyr  Thr  Thr  Lys  Glu
                  260                      265                      270

Ile  Phe  Arg  Lys  Asn  Phe  Phe  Lys  Asp  Trp  Arg  Lys  Glu  Met  Thr  Asn
              275                      280                      285

Glu  Glu  Lys  Asn  Ile  Ile  Thr  Asn  Leu  Ser  Lys  Cys  Asp  Phe  Thr  Gln
     290                      295                      300

Met  Ser  Gln  Tyr  Phe  Lys  Ala  Gln  Thr  Glu  Ala  Arg  Lys  Gln  Met  Ser
305                      310                      315                      320
```

| Lys | Glu | Glu | Lys | Leu<br>325 | Lys | Ile | Lys | Glu<br>330 | Glu | Asn | Glu | Lys | Leu<br>335 | Leu | Lys |
|---|---|---|---|---|---|---|---|---|---|---|---|---|---|---|---|
| Glu | Tyr | Gly | Phe<br>340 | Cys | Ile | Met | Asp | Asn<br>345 | His | Lys | Glu | Arg | Ile<br>350 | Ala | Asn |
| Phe | Lys | Ile<br>355 | Glu | Pro | Pro | Gly<br>360 | Leu | Phe | Arg | Gly | Arg<br>365 | Gly | Asn | His | Pro |
| Lys | Met<br>370 | Gly | Met | Leu | Lys<br>375 | Arg | Arg | Ile | Met<br>380 | Pro | Glu | Asp | Ile | Ile | Ile |
| Asn<br>385 | Cys | Ser | Lys | Asp<br>390 | Ala | Lys | Val | Pro | Ser<br>395 | Pro | Pro | Gly | His | Lys<br>400 | |
| Trp | Lys | Glu | Val | Arg<br>405 | His | Asp | Asn | Lys | Val<br>410 | Thr | Trp | Leu | Val | Ser<br>415 | Trp |
| Thr | Glu | Asn | Ile | Gln<br>420 | Gly | Ser | Ile | Lys | Tyr<br>425 | Ile | Met | Leu | Asn | Pro<br>430 | Ser |
| Ser | Arg | Ile<br>435 | Lys | Gly | Glu | Lys<br>440 | Asp | Trp | Gln | Lys | Tyr<br>445 | Glu | Thr | Ala | Arg |
| Arg | Leu<br>450 | Lys | Lys | Cys | Val<br>455 | Asp | Lys | Ile | Arg | Asn<br>460 | Gln | Tyr | Arg | Glu | Asp |
| Trp<br>465 | Lys | Ser | Lys | Glu | Met<br>470 | Lys | Val | Arg | Gln | Arg<br>475 | Ala | Val | Ala | Leu | Tyr<br>480 |
| Phe | Ile | Asp | Lys | Leu<br>485 | Ala | Leu | Arg | Ala | Gly<br>490 | Asn | Glu | Lys | Glu | Glu<br>495 | Gly |
| Glu | Thr | Ala | Asp<br>500 | Thr | Val | Gly | Cys | Cys<br>505 | Ser | Leu | Arg | Val | Glu<br>510 | His | Ile |
| Asn | Leu | His<br>515 | Pro | Glu | Leu | Asp<br>520 | Gly | Gln | Glu | Tyr | Val<br>525 | Val | Glu | Phe | Asp |
| Phe | Leu<br>530 | Gly | Lys | Asp | Ser<br>535 | Ile | Arg | Tyr | Tyr | Asn<br>540 | Lys | Val | Pro | Val | Glu |
| Lys<br>545 | Arg | Val | Phe | Lys | Asn<br>550 | Leu | Gln | Leu | Phe | Met<br>555 | Glu | Asn | Lys | Gln | Pro<br>560 |
| Glu | Asp | Asp | Leu | Phe<br>565 | Asp | Arg | Leu | Asn | Thr<br>570 | Gly | Ile | Leu | Asn | Lys<br>575 | His |
| Leu | Gln | Asp | Leu<br>580 | Met | Glu | Gly | Leu | Thr<br>585 | Ala | Lys | Val | Phe | Arg<br>590 | Thr | Phe |
| Asn | Ala | Ser<br>595 | Ile | Thr | Leu | Gln<br>600 | Gln | Leu | Lys | Glu | Leu<br>605 | Thr | Ala | Pro | |
| Asp | Glu<br>610 | Asn | Ile | Pro | Ala<br>615 | Lys | Ile | Leu | Ser | Tyr<br>620 | Asn | Arg | Ala | Asn | Arg |
| Ala<br>625 | Val | Ala | Ile | Leu | Cys<br>630 | Asn | His | Gln | Arg | Ala<br>635 | Pro | Pro | Lys | Thr | Phe<br>640 |
| Glu | Lys | Ser | Met | Met<br>645 | Asn | Leu | Gln | Thr | Lys<br>650 | Ile | Asp | Ala | Lys | Lys<br>655 | Glu |
| Gln | Leu | Ala | Asp<br>660 | Ala | Arg | Arg | Asp | Leu<br>665 | Lys | Ser | Ala | Lys | Ala<br>670 | Asp | Ala |
| Lys | Val | Met<br>675 | Lys | Asp | Ala | Lys | Thr<br>680 | Lys | Lys | Val | Val | Glu<br>685 | Ser | Lys | Lys |
| Lys | Ala<br>690 | Val | Gln | Arg | Leu | Glu<br>695 | Glu | Gln | Leu | Met | Lys<br>700 | Leu | Glu | Val | Gln |
| Ala | Thr | Asp | Arg | Glu | Glu | Asn | Lys | Gln | Ile | Ala | Leu | Gly | Thr | Ser | Lys |
| 705 | | | | | 710 | | | | 715 | | | | | | 720 |
| Leu | Asn | Phe | Leu | Asp<br>725 | Pro | Arg | Ile | Thr | Val<br>730 | Ala | Trp | Cys | Lys | Lys<br>735 | Trp |
| Gly | Val | Pro | Ile<br>740 | Glu | Lys | Ile | Tyr | Asn<br>745 | Lys | Thr | Gln | Arg | Glu<br>750 | Lys | Phe |

```
Ala  Trp  Ala  Ile  Asp  Met  Ala  Asp  Glu  Asp  Tyr  Glu  Phe
          755                 760                      765
```

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "PR1 primer of Scl-70"

( x i ) SEQUENCE DESCRIPTION: SEQ ID NO:3:

```
GATCCTAGGG  TCCAGAAAAT  TGAG                                    24
```

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "PF1 primer of Scl-70"

( x i ) SEQUENCE DESCRIPTION: SEQ ID NO:4:

```
AAGGAACAGC  TAGCAGATGC  CCGG                                    24
```

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "N8 primer"

( x i ) SEQUENCE DESCRIPTION: SEQ ID NO:5:

```
CTTGCAAACT  AAGATTG                                             17
```

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "PR2 primer of Scl-70"

( x i ) SEQUENCE DESCRIPTION: SEQ ID NO:6:

```
CCGGGCATCT  GCTAGCTGTT  CCTT                                    24
```

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
( A ) DESCRIPTION: /desc = "PF2 primer of Scl-70"

( x i ) SEQUENCE DESCRIPTION: SEQ ID NO:7:

AAGGTATTCC GTACGTTCAA TGCC  2 4